United States Patent [19]

Farng et al.

[11] Patent Number: 5,681,798

[45] Date of Patent: Oct. 28, 1997

[54] LOAD-CARRYING ADDITIVES BASED ON ORGANO-PHOSPHITES AND AMINE PHOSPHATES

[76] Inventors: Liehpao O. Farng, 15 Yiger Dr., Lawrenceville, N.J. 08648; William F. Olszewski, 42 Knollwood Dr., Cherry Hill, N.J. 08002

[21] Appl. No.: 708,062

[22] Filed: Aug. 1, 1996

[51] Int. Cl.[6] ............................................. C10M 137/12

[52] U.S. Cl. .......................... 508/425; 508/423; 558/155; 558/158; 558/163

[58] Field of Search ......................... 508/423, 425; 558/155, 158, 163

[56] References Cited

U.S. PATENT DOCUMENTS

| | | | |
|---|---|---|---|
| 3,014,954 | 12/1961 | Birum | 508/423 |
| 3,042,701 | 7/1962 | Birum | 508/423 |
| 3,042,702 | 7/1962 | Birum | 508/423 |
| 3,197,405 | 7/1965 | LeSuer . | |
| 3,197,496 | 7/1965 | LeSuer . | |
| 3,534,125 | 10/1970 | Knollmueller | 508/423 |
| 4,155,958 | 5/1979 | Fields . | |
| 4,435,338 | 3/1984 | Michaelis et al. . | |
| 4,697,030 | 9/1987 | Hardy et al. | 558/163 |
| 5,256,320 | 10/1993 | Todd et al. | 508/423 |
| 5,347,029 | 9/1994 | Johnson | 558/158 |
| 5,500,140 | 3/1996 | Hughes et al. | 558/158 |
| 5,593,492 | 1/1997 | Schaffer et al. | 106/623 |

Primary Examiner—Ellen M. McAvoy

[57] ABSTRACT

Lubricant and fuel compositions containing a small additive concentration of a novel organo-phosphorus composition based on phosphite-derived hydroxyl compounds and amine phosphates possess excellent antiwear properties coupled with good extreme pressure activities. Additional antioxidation, cleanliness, antifatigue, high temperature stabilizing, and friction modifying properties are expected. Both the phosphite-hydroxy moiety and the amine phosphate moiety are believed to provide the basis for the synergistic antiwear and EP property of these novel additives.

25 Claims, No Drawings

LOAD-CARRYING ADDITIVES BASED ON ORGANO-PHOSPHITES AND AMINE PHOSPHATES

FIELD OF THE INVENTION

This invention is directed to hydrocarbyl phosphite derived amine phosphites which are useful as multifunctional antioxidation, antiwear, and anticorrosion lubricant additives and to a process for making said additives as well as to lubricant compositions comprised thereof.

BACKGROUND OF THE INVENTION

Use of phosphites, such as dibutyl phosphite bis(tridecyl) phosphite, bis(2-ethylhexyl) phosphite, dilauryl phosphite and dioleyl phosphite, has been widely reported for their load-carrying and anti-chattering properties in lubricants.

Amines have been used in the lubricants and detergent industry for their alkalinity, surface activity, and neutralization capability. Amine phosphate is one class of additives used extensively in industrial oils. Polyamine-derived succinimides are key components in ashless dispersants of engine oils. The use of amine derivatives, such as amine phosphate salts, has been widespread for several decades as corrosion inhibitors and antiwear/EP additives.

Benzotriazole or substituted benzotriazole compounds reacted with an alkyl aldehyde and dialkylhydrogen phosphites provide products which improve the load-carrying, antiwear properties of lubricant oils and greases. These reactants are disclosed in U.S. Pat. No. 4,626,368 which issued to Cardis on Dec. 2, 1986. Amine coupled condensation products of hindered phenols and phosphites are disclosed in U.S. Pat. No. 5,288,418 which issued to Farng et al. on Feb. 22, 1994. These products were found to be effective antioxidant/antiwear additives for lubricants. These patents are incorporated by reference herein.

Dibutyl phosphite is mentioned as a functional additive in U.S. Pat. No. 5,354,484 which issued to Schwind et al. as an inhibitor for metal corrosion. However, nothing in this patent suggests use of a dihydrocarbyl amine phosphate alone for use as a multifunctional antiwear, antioxidant, and anticorrosion lubricant additive.

Alkoxylated amine phosphite adducts are disclosed as lube additives in U.S. Pat. No. 5,071,577 which issued to Benjamin et al. Nothing in this patent suggests use of a dihydrocarbyl amine phosphate as a multifunctional antiwear, antioxidant, anticorrosion lubricant additive.

U.S. Pat. No. 4,612,128 which issued to Uematsu et al. discloses a lubricating composition comprising (a) a lubricating oil, (b) at least one phosphite ester of pentaerythritol, and (c) at least one compound selected from phosphate monoesters and diesters and phosphonates. This composition is suitable for metal forming, particularly for plastic working of aluminum and aluminum alloys for formability and heat resistance. A dihydrocarbyl amine phosphate multifunctional lubricant additive with antiwear, antioxidant, and anticorrosion characteristics is not suggested.

Mixed neutralized phosphates for improvement of the extreme pressure properties of a lubricant are disclosed by Salentine in U.S. Pat. No. 4,575,431. Although dihydrocarbyl hydrogen dithiophosphates combined with a sulfur-free mixture of hydrocarbyldihydrogen phosphates and dihydrocarbyl hydrogen phosphates are disclosed, nothing in this patent suggests use of a singular dihydrocarbyl amine phosphate as a multifunctional antiwear, antioxidant, anticorrosion lubricant additive.

Alkyl and aryl phosphates or phosphites are disclosed as lube additives in U.S. Pat. No. 4,514,312 which issued to Root et al. These phosphates or phosphites are combined with one or more oil-insoluble, sulfur-free inorganic phosphates to impart extreme pressure properties to a lubricant composition. However, nothing in this patent suggests use of a dihydrocarbyl amine phosphate alone as a multifunctional antiwear, antioxidant, anticorrosion lubricant additive.

Amine phosphate salts useful as lube additives are disclosed in U.S. Pat. No. 4,118,328 which issued to Hotten. Although use of a triaryl phosphate is mentioned, nothing in this patent suggests use of a dihydrocarbyl amine phosphate as a multifunctional antiwear, antioxidant, and anticorrosion lubricant additive.

It has now been found that combinations of phosphite and amine phosphate chemistry provide exceptional antiwear/EP activity with significantly enhanced metal passivating and corrosion inhibiting properties.

SUMMARY OF THE INVENTION

It has been found that lubricant and fuel compositions containing a small additive concentration of a novel organo-phosphorus composition based on phosphite-derived hydroxyl compounds and amine phosphates possess excellent antiwear properties coupled with good extreme pressure activities. Additional antioxidation, cleanliness, antifatigue, high temperature stabilizing, and friction modifying properties are also expected with many of the disclosed composition of the instant invention. Both the phosphite-hydroxy moiety and the amine phosphate moiety are believed to provide a basis for the synergistic antiwear and EP properties of these novel additives.

All of these beneficial properties are believed to be enhanced as a result of this novel internal synergism. This unique internal synergism is believed to be applicable to similar structures containing (a) phosphite groups, (b) phosphate groups, and (c) amine groups within the same component. Products containing additives resultant from these compositions display good stability and compatibility when used in the presence of other commonly used additives in fuel or lubricant compositions.

Accordingly, this invention is directed to lubricant compositions comprising a major amount of an oil of lubricating viscosity and a minor multifunctional amount of the herein described novel organo-phosphorus composition based on phosphite-derived hydroxyl compounds and amine phosphates.

It is therefore an object of this invention to provide improved lubricant compositions comprising the aforementioned multifunctional additive reaction products.

BRIEF DESCRIPTION OF THE PREFERRED EMBODIMENTS

Dihydrocarbyl phosphites, such as dibutyl phosphite or diphenyl phosphite, were reacted with aldehydes/ketones in the absence of a catalyst at elevated temperatures under various ratios to form phosphonate-derived alcohols as generally described in equation 1 (Eqn 1) below:

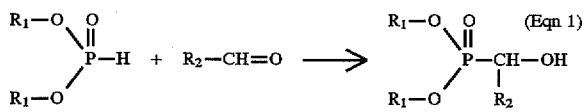

where $R_1$ is $C_1$ to $C_{60}$ hydrocarbyl and $R_2$ is hydrogen or $C_1$ to $C_{30}$ hydrocarbyl. Although not shown in Eqn. 1, the reaction can also be carried out by using catalytic amounts of a catalyst. A preferred catalyst for use herein comprises one selected from a hydroxide of an alkali metal or an alkaline-earth metal. Of these sodium hydroxide, potassium hydroxide, calcium hydroxide, and lithium hydroxide are preferred.

In step 2 below, the phosphonate-derived alcohols were further reacted with phosphorus pentoxide to form phosphoric acids. These acids are subsequently neutralized with amines in step 3 to form amine phosphates. Step 2 is represented by equation 2 (Eqn 2) below:

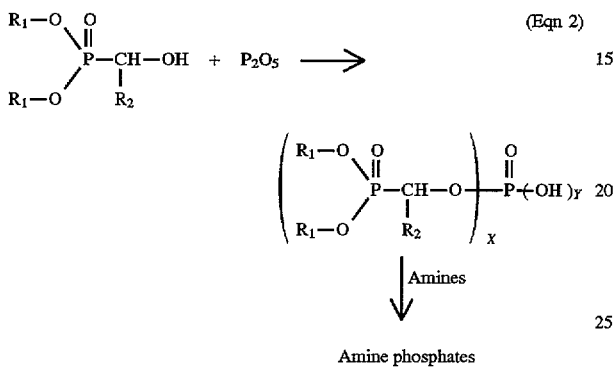

where X is 1 to 2 and X+Y=3.

An excess of one reagent or another can be used. Molar quantities, less than molar quantities, or more than molar quantities of either phosphite or aldehyde in the first step, either alcohol or $P_2O_5$ in the second step, either phosphoric acid or amine in the third step can be used.

A variety of alkyl and arylamines can be used. Specifically, a branched secondary amine, or a branched primary etheramine, or a branched alkyl diamine, or a branched t-alkyl primary amine can be used.

Examples of the above-mentioned amines which are preferred for use herein are selected from a member of the group consisting of isotridecyloxypropylamine (Tradename: PA-17), N-oleyl-1,3-diaminopropane, bis(2-ethylhexyl) amine and $C_8$ to about $C_{22}$ amines (such as Röhm Haas products sold under the trade name PRIMENE 81R and PRIMENE J-MT). PRIMENE 81R is a $C_{11}$ to $C_{13}$ t-alkyl primary amine.

Other examples of aliphatic primary, secondary or tertiary amines which can be utilized herein are:

a) cyclic amines e.g. dicyclohexylamine, 1,4-diaminocyclohexane, piperidine, hexamethyleneimine, and others having 3–60 carbon atoms, and more preferably 8 to 30 carbon atoms;

b) heterocyclic amines such as morpholine, aminopropyl morpholine (APM), aminoethyl piperazine (AEP) and others having 3 to 60 carbon atoms, preferably those having 4 to 30 carbon atoms;

c) alkyloxyhydrocarbylamines such as EXXON $C_6$ to $C_{15}$ alky loxypropyl amines sold under the PA-10, PA-1214, PA-14, PA-17 and PA-19 trademarks; WITCO $C_{10}$ to $C_{13}$ alkyloxypropylamines sold under the ADOGEN 180 and ADOGEN 183 trademarks; and Texaco polyether primary amines derived from nonylphenol ethoxylates that are sold under the tradename SURFONAMINE MNPA and represented by the following formula:

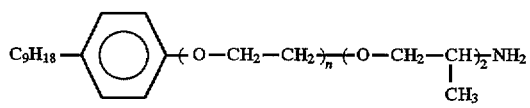

where n = 0–60;

d) diamines such as Exxon DA-14, DA-17, etherdiamines an d Akzo's DUOMEEN diamines such as DUOMEEN C and DUOMEEN O (N-oleyl-1,3-diaminopropane) that are represented by the following formulas and structure;

$R-NH-CH_2CH_2NH_2$ or $R-N-CH_2CH_2CH_2N(CH_3)_2$
     |
     $CH_3$ or

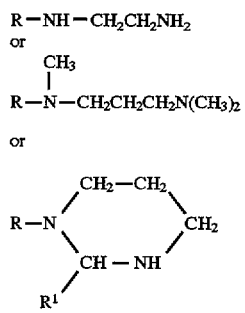

where R and $R^1$ are $C_3$ to $C_{60}$ hydrocarbyl;

e) straight chain amines which include ethylamine, prop ylamine, butylamine, pentylamine, hexylamine, decylamine, dioctylamine, dicocoamine, and other $C_2$ to $C_{60}$ amines where $C_8$ to $C_{30}$ amines are preferred;

f) branched chain amines such as 2-ethylamine, isopropylamine, isobutylamine, diisobutylamine, bis (2-ethylhexyl) amine, and ARMEEN HTL8 2-ethylhexyl hydrogenated tallow amine and other $C_2$ to $C_{60}$ amines where $C_2$ to $C_{30}$ amines are preferred;

g) tertiary amines such as tri(n-butyl) amine as well as trialkyl fatty amines that are sold under the ARMEEN DMCD, ADOGEN DA-100 and ADOGEN 364 & 369 trademarks which have the following formulas:

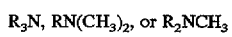

which are tertiary amines trialkyls, tertiary amines monoalkyls, or tertiary amines dialkyls respectively where $R_1$, $R_2$, and $R_3$ are $C_3$ to $C_{60}$ hydrocarbyl, and as is preferred $C_4$ to $C_{30}$ hydrocarbyl; and h) alkoxylated amines such as ETHOMEEN T/12, and ETHOMEEN 0/12 amines that are represented by the following formulas for ethoxylated amines, ethoxylated diamines, and propoxylated amines respectively;

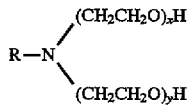

where R is $C_3$ to $C_{60}$ hydrocarbyl and x+y=2, 5, 10, 15 or 50;

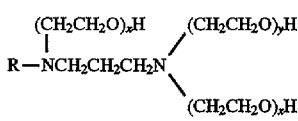

where R is $C_3$ to $C_{60}$ hydrocarbyl and $x+y+z=3$, 10, or 15; and

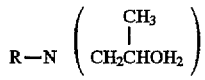

where R is $C_3$ to $C_{60}$ hydrocarbyl.

Other alkoxylated amines that can be used include butoxylated, pentoxylated, and hexoxylated amines. Alkoxylated amines and amine phosphites are described in U.S. Pat. No. 4,557,845 which is incorporated herein by reference.

Suitable aldehydes or ketones which can be used herein have the following general formula:

where n is a number from 1 to 20.

Representative ketones which can be utilized herein include but are not limited to the following: methylethylketone (2-butanone), acetone, 2-pentanone, 3-pentanone, 3-methyl-2-butanone, 2,4-dimethyl-3-pentanone, 4,4-dimethyl-2-pentanone, 2-heptanone, 3-heptanone, 4-heptanone, 2-methyl-3-hexanone, 5-methyl-2-hexanone, 2-methyl-3-heptanone, 5-methyl-3-heptanone, 2-octanone, 3-octanone, 2-nonanone, 3-nonanone, 5-nonanone, 2,2,-4,4-tetramethyl-3-pentanone, 2,6-dimethyl-4-heptanone, 2-decanone, 3-decanone, and 4-decanone. Other $C_1$ to $C_{20}$ ketones and isomers thereof can also be used.

Aldehydes which can be used include, but are not limited to, formaldehyde, acetaldehyde, propionaldehyde, butyraldehyde, isobutyraldehyde, valeraldehyde, trimethylacetaldehyde, 2-methyl butyraldehyde, heptaldehyde, 2,3-dimethylvaleraldehyde, 2-ethylhexanal, octylaldehyde, nonyl aldehyde, and decyl aldehyde. Other $C_1$ to $C_{20}$ aldehydes and isomers thereof can also be used. Paraformaldehyde is a preferred carbonyl coupling agent for use herein. Of the alkyl aldehydes, butyraldehyde and 2-ethylhexanal are preferred.

Generally speaking, conditions for the above described reactions may vary widely depending upon specific reactants, the presence or absence of a solvent and the like. Any suitable set of reaction conditions known to the art may be used. Generally, stoichiometric quantities of reactants are used. However, equimolar, more than molar or less than molar amounts may be used. An excess of up to 100% or more of any of the reactants can be used. Preferably, the molar ratio of reactants varies from about 10:50:3:1:100 moles to about 5:1:0.3:0.1:0.1 moles respectively of phosphite, aldehyde, $P_2O_5$, mixed phosphoric acid, and amine. The reaction temperature may vary from ambient to about 350° C. or reflux, the pressure may vary from ambient or autogenous to about 1,000 psi.

The additives embodied herein are utilized in lubricating oil or grease compositions in an amount which imparts significant antiwear characteristics to the oil or grease as well as reducing the friction of engines operating with the oil in its crankcase. Concentrations of about 0.001 to about 10 wt % based on the total weight of the composition can be used. Preferably, the concentration is from 0.1 to about 3 wt. %.

The additives have the ability to improve the above noted characteristics of various oleaginous materials such as hydrocarbyl lubricating media which may comprise liquid oils in the form of either a mineral oil or a synthetic oil, or in the form of a grease in which the aforementioned oils are employed as a vehicle.

In general, mineral oils, both paraffinic, naphthenic and mixtures thereof, employed as the lubricant, or grease vehicle, may be of any suitable lubricating viscosity range, as for example, from about 45 SUS at 100° F. to about 6,000 SUS at 100° F. and preferably, from about 50 to about 250 SUS at 210° F. These oils may have viscosity indexes preferably ranging to about 95. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps, which are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any material which is normally employed for thickening or gelling hydrocarbon fluids for forming grease can be used in preparing grease in accordance with the present invention.

In instances where synthetic oils, or synthetic oils employed as the lubricant or vehicle for the grease, are desired in preference to mineral oils, or in combination therewith, various compounds of this type may be successfully utilized. Typical synthetic oils include, but are not limited to, synthetic liquid hydrocarbons such as the polyolefin derivatives, especially the hydrogenated polyolefins such as the polyisobutylenes, polybutenes, and the hydrogenated poly alpha-olefins (PAOs) including, especially, the hydrogenated polydecenes; the polyglycols or polyalkylene glycols (PAGs) such as polypropylene glycol and polyethylene glycol, synthetic esters such as the esters of dibasic aliphatic or aromatic carboxylic acids and monohydric alcohols such as di(2-ethylhexyl) sebacate, di(2-ethylhexyl) adipate and dibutyl phthalate and the esters of polyhydric alcohols and monobasic carboxylic acids such as the neopentyl polyol esters of monocarboxylic acids, including the neopentyl glycol, trimethylolpropane and pentaerythritol (mono- and di-pentaerythritol) esters of acids such as the $C_5$–$C_{20}$ monocarboxylic acids including the straight and branched chain acids, especially the $C_5$–$C_{12}$ straight and branched chain acids and mixtures of these acids. Synthetic lubricating fluids of these and other less common types such as the fluorocarbons, esters of phosphorus-containing acids, siloxanes and silicones (polysiloxanes), alkyl-substituted diphenyl ethers typified by a butyl-substituted bis(p-phenoxy phenyl) ether, and phenoxy phenylethers, are described in "Synthetic Lubricants" Gunderson & Hart, Reinhold Publ. Corp. 1962, to which reference is made for a description of these materials. Additional synthetic fluids or vehicles appear in U.S. Pat. Nos. 5,348,674 and 5,338,470 which issued to Blain et al. on Sep. 20, 1994 and to Hiebert et al. on Aug. 16, 1994, respectively. These patents are incorporated by reference herein in their entireties.

It is to be understood, however, that the compositions contemplated herein can also contain other materials. For example, corrosion inhibitors, extreme pressure agents, low temperature properties modifiers and the like can be used as exemplified respectively by metallic phenates or sulfonates, polymeric succinimides, non-metallic or metallic phosphorodithioates and the like. These materials do not detract from the value of the compositions of this invention, rather the materials serve to impart their customary properties to the particular compositions in which they are incorporated.

The additives in accordance with the invention are believed to be highly useful in fuel compositions, particularly in liquid hydrocarbon fuels or oxygenated fuels such as alcoholic fuels and the like and mixtures thereof. The present additives are used in fuel compositions in amounts ranging from about 1 to about 1,000 pounds of additive per 1,000 barrels of fuel and preferably from about 10 to about 250 pounds per 1,000 pounds of fuel. In addition to liquid hydrocarbon and oxygenated combustion fuels, distillate fuels and fuel oils are also contemplated.

The following examples are merely illustrative and are not meant to be limitations.

EXAMPLE 1

Reaction Product of Dibutyl Phosphite and Butyraldehyde

Into a four-necked flask equipped with a stirrer, condenser, an inert nitrogen inlet and a thermometer were added 404 grams (2.08 moles) of 96% purity grade dibutyl phosphite and 144 grams (2.0 moles) of butyraldehyde. This reaction mixture was stirred at room temperature for two hours, then at 60° C. for two hours, then at 80° C. for two hours, and finally at 110° C. for two hours. This provided 548 grams of a clear, light brown fluid at 100% yield.

EXAMPLE 2

Reaction Product of Dibutyl Phosphite and Butyraldehyde

Into a four-necked flask equipped with a stirrer, condenser, an inert nitrogen inlet and thermometer were added 812 grams (4.18 moles) of 96% purity grade dibutyl phosphite and 289 grams (4.0 moles) of butyraldehyde. This reaction mixture was stirred at room temperature for two hours, then at 60° C. for two hours, then at 80° C. for two hours, and finally at 110° C. for twelve hours. This provided 1,097 grams of a clear, light brown fluid at 99.6% yield.

EXAMPLE 3

Dibutyl Phosphite-Butyraldehyde Derived Mixed Phosphoric Acids

Approximately 1,097 grams (4.0 moles) of the above product of Example 2 was placed in a four-necked flask. Slowly, 189.5 grams (1.33 moles) of phosphorus pentoxide was added portion wise to the reactor over a course of two hours. The moderate exotherm carried the reaction temperature up to about 55° C. and the reaction mixture was very hazy. It was further reacted at 70° C. for one hour, then at 80° C. for two additional hours until the reaction mixture became clear. This produced 1,280 grams of crude phosphoric acids. After a quick filtration, approximately 1,260 grams of a brownish fluid was recovered as desired product.

EXAMPLE 4

Dibutyl Phosphite Derived Phosphoric Acid—t-Alkyl Primary Amine

Approximately 94.0 grams (0.1 mole) of the above product of Example 3 and 84 grams (0.3 mole) of a commercial, branched t-alkyl primary amine (available from Röhm H aas Chemical Company under the trade name "PRIMENE JM-T", composed of amines with an alkyl chain length principally in the $C_{18}$ to $C_{22}$ range) were charged in a four-necked flask. The moderate exotherm carried the reaction temperature up to about 55° C., and the reaction mixture was further reacted at 80° C. for one hour, then it was filtered while hot. This produced 178 grams of amine phosphates as desired products.

EXAMPLE 5

Dibutyl Phosphite Derived Phosphoric Acid—t-Alkyl Primary Amine

Approximately 94.0 grams (0.1 mole) of the above product of Example 3 and 56 grams (0.2 mole) of a commercial, branched t-alkyl primary amine (available from Röhm H aas Chemical Company under the trade name "PRIMENE JM-T", composed of amines with an alkyl chain length principally in the $C_{18}$ to $C_{22}$ range) were charged in a four-necked flask. The moderate exotherm carried the reaction temperature up to about 55° C., and the reaction mixture was further reacted at 80° C. for one hour, then it was filtered while hot. This produced 140 grams of amine phosphates as desired products.

EXAMPLE 6

Dibutyl Phosphite Derived Phosphoric Acid—Etheramine Salts

The reaction procedure of Example 4 was followed with one exception: an equimolar amount of isotridecyloxypropylamine (commercially available from Witco-Sherex Chemical Company under the trade name: "ADOGEN 183" or from Exxon Chemical—"TOMAH" under the trade name: PA-17) was used instead of "PRIMENE JM-T."

EXAMPLE 7

Dibutyl Phosphite Derived Phosphoric Acid—Etheramine Salts

The reaction procedure of Example 5 was followed with one exception: an equimolar amount of isotridecyloxypropylamine (commercially available from Witco-Sherex Chemical Company under the trade name: "ADOGEN 183" or from Exxon Chemical—"TOMAH" under the trade name: PA-17) was used instead of "PRIMENE JM-T."

EXAMPLE 8

Dibutyl Phosphite Derived Phosphoric Acid—Oleyl Diamine Salts

The reaction procedure of Example 4 was followed with the following exception: one half molar N-oleyl-1,3-diaminopropane (commercially available from Akzo Chemical Company under the trade name: "DUOMEEN O") was used instead of "PRIMENE JM-T."

EXAMPLE 9

Dibutyl Phosphite Derived Phosphoric Acid—Oleyl Diamine Salts

The reaction procedure of Example 5 was followed with the following exception: one half molar N-oleyl-1,3- diaminopropane (commercially available from Akzo Chemical Company under the trade name: "DUOMEEN O") was used instead of "PRIMENE JM-T."

EXAMPLE 10

Dibutyl Phosphite Derived Phosphoric Acid—Bis (2-ethylhexyl)amine Salts

Approximately 128.7 grams (0.137 mole) of the above product of Example 3 and 96.66 grams (0.4 mole) of bis(2-ethylhexyl) amine were charged in a four-necked flask. The moderate exotherm carried the reaction temperature up to about 55° C., and the reaction mixture was further reacted at 80° C. for two hours, then it was filtered while hot. This produced 225 grams of amine phosphates as desired products.

EXAMPLE 11

Dibutyl Phosphite Derived Phosphorus Acid—Oleyl Diamine Salts

Approximately 128.7 grams (0.137 mole) of the above product of Example 3 and 66 grams (0.2 mole) of N-oleyl-1,3-diaminopropane ("DUOMEEN O") were charged in a four-necked flask. The moderate exotherm carried the reaction temperature up to about 55° C., and the reaction mixture was further reacted at 90° C. for two hours, then it was filtered while hot. This produced 194 grams of amine phosphates as desired products.

EXAMPLE 12

Dibutyl Phosphite Derived Phosphoric Acid—Bis (2-ethylhexyl)amine Salts

Approximately 158.0 grams (0.168 mole) of the above product of Example 3 and 80.5 grams (0.333 mole) of bis(2-ethylhexyl) amine were charged in a four-necked flask. The moderate exotherm carried the reaction temperature up to about 55° C., and the reaction mixture was further reacted at 70° C. for two hours, then it was filtered while hot. This produced 235 grams of amine phosphates as desired products.

EXAMPLE 13

Reaction Product of Dibutyl Phosphite and 2-Ethylhexanal

Into a four-necked flask equipped with a stirrer, condenser, an inert nitrogen inlet and thermometer were added 606 grams (3.12 moles) of 96% purity grade dibutyl phosphite and 384 grams (3.0 moles) of 2-ethyhexanal. This reaction mixture was stirred at room temperature for two hours, then at 100° C. for three hours, and finally at 120° C. for seven hours. This provided 990 grams of a clear, light brown fluid at 100% yield.

EXAMPLE 14

Dibutyl Phosphite/2-Ethylhexanal Derived Mixed Phosphoric Acids

Approximately 990 grams (3.0 moles) of the above product of Example 13 was placed in a our-necked flask. Slowly, 143 grams (1.0 moles) of phosphorus pentoxide was added portion wise to the reactor over a course of two hours. The moderate exotherm carried the reaction temperature up to about 50° C. and the reaction mixture was very hazy. It was further reacted at 70° C. for one hour, then at 80° C. for one hour, and finally at 100° C. for two additional hours until the reaction mixture became clear. After a quick filtration, approximately 1,122 grams of a brownish fluid was recovered as desired product.

EXAMPLE 15

Dibutyl Phosphite Derived Phosphoric Acid—Oleyl Diamine Salts

Approximately 226.6 grams (0.2 mole) of the above product of Example 14 and 98 grams (0.3 mole) of N-oleyl-1,3-diaminopropane ("DUOMEEN O") were charged in a four-necked flask. The moderate exotherm carried the reaction temperature up to about 72° C., and the reaction mixture was further reacted at 90° C. for two hours, then it was filtered while hot. This produced 324 grams of amine phosphates as desired products.

The products of the Examples were blended in mineral oils and evaluated for antiwear performance using the Four-Ball test (Table 1) below.

EVALUATION OF PRODUCTS

The product of the above Examples was blended into a base oil and evaluated for antiwear performance using the Four-Ball test (ASTM Method D-2266, Table 1).

TABLE 1

FOUR-BALL WEAR TEST

| Item | Wear Scar Diameter in MM, 30 Minute Test | | |
|---|---|---|---|
| | 93° C. 40 Kg 1,800 rpm | 93° C. 60 Kg 1,500 rpm | 135° C. 60 Kg 100 rpm |
| Base oil (80% solvent paraffinic bright, 20% solvent paraffinic neutral mineral oils) | 0.733 | 2.12 | 0.47 |
| 1% Example 4 | 0.336 | 0.500 | 0.373 |
| 1% Example 5 | 0.422 | 0.542 | 0.397 |
| 1% Example 6 | 0.391 | 0.472 | 0.368 |
| 1% Example 7 | 0.412 | 0.467 | 0.383 |
| 1% Example 8 | 0.469 | 0.578 | 0.386 |
| 1% Example 10 | 0.346 | 0.484 | 0.367 |
| 1% Example 11 | 0.396 | 0.428 | 0.356 |
| 1% Example 12 | 0.349 | 0.441 | 0.383 |
| 1% Example 15 | 0.367 | 0.422 | 0.374 |

As can be seen from the above wear test results, the product exhibits considerable antiwear activity in various conditions.

INTERPRETATION OF TEST RESULTS

The use of this new class of phosphite-derived amine phosphates in premium quality lubricants will significantly enhance stability, improve load-carrying, reduce wear, and extend service life. These additives may also have the potential to benefit gasoline and diesel fuels by improving the antioxidation, antiwear, and anticorrosion characteristics of these fuels. These novel compositions described herein are useful at low concentrations and do not contain any potentially undesirable metals or corrosive sulfur.

As shown above, the products of this invention demonstrate considerable antiwear activity as evidenced by the reduction of the wear scar diameters and the wear volume.

Although these products have demonstrated significant antiwear/EP activity, they are extremely non-corrosive to metals, such as copper alloys.

The use of additive concentrations of this invention in fuels will significantly reduce fuel pump and injector components wear problems associated with low sulfur and aromatics containing fuels. These additives potentially may also benefit fuel and lubricant properties by improving antiwear and fuel economy characteristics and extending engine life.

Although the present invention has been described with preferred embodiments, it is to be understood that modifications and variations may be resorted to, without departing from the spirit and scope of this invention, as those skilled in the art will readily understand. Such variations and modifications are considered to be within the purview and scope of the appended claims.

What is claimed:

1. An improved lubricant composition comprising a major proportion of an oil of lubricating viscosity or grease prepared therefrom and a minor amount of a multifunctional antiwear, antioxidant, anticorrosion additive product of reaction prepared by (a) reacting a dihydrocarbyl phosphite with an aldehyde or ketone to form a dihydrocarbyl phosphonate-derived alcohol; (b) thereafter reacting said dihydrocarbyl phosphonate-derived alcohol with phosphorus pentoxide thereby forming dihydrocarbyl phosphoric acids; and (c) subsequently neutralizing the dihydrocarbyl phosphoric acids with an amine thereby obtaining a dihydrocarbyl amine phosphate wherein the reaction is carried out at temperatures varying from ambient to about 350° C. under pressures from ambient up to about 1,000 psi or autogenous pressures for a time sufficient to obtain the desired dihydrocarbyl amine phosphate additive product of reaction and wherein the reaction is carried out in molar ratios of reactants varying from equimolar to more than molar to less than molar.

2. The composition of claim 1 wherein said dihydrocarbyl amine phosphate additive product is prepared in a multi-step batch or multi-step continuous process comprising reacting (a) said dihydrocarbyl phosphite and aldehyde or ketone; (b) the dihydrocarbyl phosphonate-derived alcohol and phosphorus pentoxide; and (3) the amine and the dihydrocarbyl phosphoric acid in a suitable reaction medium.

3. The composition of claim 1 wherein said dihydrocarbyl phosphoric acids have the following structure:

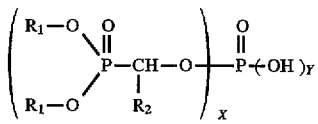

wherein $R_1$ is $C_1$ to about $C_{60}$ hydrocarbyl, $R_2$ is H or $C_1$ to about $C_{30}$ hydrocarbyl, and X is 1 to 2 and X+Y=3.

4. The composition of claim 1 wherein the reactants are dibutyl phosphite and butyraldehyde, dibutyl phosphonate-derived alcohols and phosphorus pentoxide, and a dibutyl phosphite derived phosphoric acid and a branched t-alkyl primary amine comprised of amines with an alkyl chain length of about $C_8$ to about $C_{22}$.

5. The composition of claim 1 wherein the reactants are dibutyl phosphite and butyraldehyde, dibutyl phosphonate-derived alcohols and phosphorus pentoxide, and a dibutyl phosphite derived phosphoric acid and isotridecyloxypropylamine.

6. The composition as recited in claim 1 where in step (a) said aldehyde is selected from a member of the group consisting of butyraldehyde, 2-ethylhexanal, formaldehyde, paraformaldehyde, ethylaldehyde, isobutyraldehyde, furfural, benzaldehyde, valeraldehyde, and other $C_1$ to $C_{20}$ aldehydes or isomers thereof.

7. The composition of claim 1 where in step (a) said ketone is selected from a member of the group consisting of methylethylketone (2-butanone), acetone, and other $C_1$ to $C_{20}$ ketones or isomers thereof.

8. The composition of claim 1 where in step (c) said amine is selected from a member of the group consisting of isotridecyloxypropylamine, N-oleyl-1,3-diaminopropane, and bis(2-ethyhexyl) amine.

9. The composition of claim 1 where in step (c) said amine is selected from a member of the group consisting of a branched t-alkyl primary amine comprised of amines with an alkyl chain length of about $C_8$ to about $C_{22}$, $C_3$ to $C_{60}$ cyclic amines, $C_3$ to $C_{60}$ heterocyclic amines, $C_6$ to $C_{150}$ alkyloxyhydrocarbylamines, $C_2$ to $C_{150}$ diamines, $C_2$ to $C_{60}$ straight and branched chain amines, $C_5$ to $C_{150}$ tertiary amines, and $C_8$ to $C_{150}$ alkoxylated amines.

10. The composition of claim 1 where the reactants are dibutyl phosphite, butyraldehyde, phosphorus pentoxide, and an amine selected from a member of the group consisting of a branched t-alkyl primary amine comprised of amines with an alkyl chain length of about $C_8$ to about $C_{22}$, isodecyloxypropylamine, N-oleyl-1,3-diaminopropane, or bis(2-ethylhexyl) amine.

11. The composition of claim 1 where the reactants are dibutyl phosphite, 2-ethylhexanal, phosphorus pentoxide, and N-oleyl-1,3-diaminopropane.

12. The composition of claim 1 wherein the lubricant is an oil of lubricating viscosity selected from the group consisting of (1) mineral oils, (2) synthetic oils, (3) or mixtures of mineral and synthetic oils or is (4) a grease prepared from any one of (1), (2) or (3).

13. The composition of claim 1 wherein the lubricant contains from about 0.001 to about 10 wt % based on the total weight of the composition of the additive product of reaction.

14. The composition of claim 12 wherein the lubricant is a mineral oil.

15. A process of preparing a multifunctional antioxidant, antiwear additive product prepared by (a) reacting a dihydrocarbyl phosphite with an aldehyde or ketone to form a dihydrocarbyl phosphonate-derived alcohol; (b) thereafter reacting said dihydrocarbyl phosphonate-derived alcohol with phosphorus pentoxide thereby forming dihydrocarbyl phosphoric acids; and (c) subsequently neutralizing the dihydrocarbyl phosphoric acids with an amine thereby obtaining a dihydrocarbyl amine phosphate wherein the reaction is carried out at temperatures varying from ambient to about 350° C. under pressures varying from ambient to about 1,000 psi or autogenous pressures for a time sufficient to obtain the desired additive product of reaction and wherein the reaction is carried out either in the presence of or in the absence of a catalytic amount of a catalyst and is carried out in molar ratios of reactants varying from equimolar to more than molar to less than molar.

16. The process of claim 15 wherein said dihydrocarbyl amine phosphate additive product is prepared in a multi-step batch or multi-step continuous process comprising reacting (a) said dihydrocarbyl phosphite and aldehyde or ketone; (b) the dihydrocarbyl phosphonate-derived alcohol and phosphorus pentoxide; and (3) the amine and the dihydrocarbyl phosphoric acid in a suitable reaction medium.

17. The process of claim 15 wherein the reactants are dibutyl phosphite and butyraldehyde, dibutyl phosphonate-derived alcohols and phosphorus pentoxide, and a dibutyl phosphite derived phosphoric acid and a branched t-alkyl primary amine comprised of amines with an alkyl chain length of about $C_8$ to about $C_{22}$.

18. The process of claim 15 wherein the reactants are dibutyl phosphite and butyraldehyde, dibutyl phosphonate-derived alcohols and phosphorus pentoxide, and a dibutyl phosphite derived phosphoric acid and isotridecyloxypropylamine.

19. A multifunctional antiwear/antioxidant lubricant additive product of reaction prepared by (a) reacting a dihydrocarbyl phosphite with an aldehyde or ketone to form a dihydrocarbyl phosphonate-derived alcohol; (b) thereafter reacting said dihydrocarbyl phosphonate-derived alcohol with phosphorus pentoxide thereby forming dihydrocarbyl phosphoric acids; and (c) subsequently neutralizing the dihydrocarbyl phosphoric acids with an amine thereby obtaining a dihydrocarbyl amine phosphate wherein the reaction is carried out at temperatures varying from ambient to about 350° C. under pressure varying from ambient to about 1,000 psi or autogenous pressures for a time sufficient to obtain the desired additive product of reaction and wherein the reaction is carried out in molar ratios of reactants varying from equimolar to more than molar to less than molar.

20. The additive product of claim 19 wherein all the reactants are reacted in a multi-step batch or multi-step continuous process.

21. An additive product of reaction of claim 19 wherein the reactants are dibutyl phosphite and butyraldehyde, dibutyl phosphonate-derived alcohols and phosphorus pentoxide, and a dibutyl phosphite derived phosphoric acid and a branched t-alkyl primary amine comprised of amines with an alkyl chain length of about $C_8$ to about $C_{22}$.

22. The additive product of reaction of claim 19 wherein the reactants are dibutyl phosphite and butyraldehyde, dibutyl phosphonate-derived alcohols and phosphorus pentoxide, and a dibutyl phosphite derived phosphoric acid and a branched t-alkyl primary amine which amine is selected from a member or the group consisting of isotridecyloxypropylamine, N-oleyl-1,3-diaminopropane, and bis(2-ethyhexyl) amine.

23. A multifunctional antiwear, antioxidant, anticorrosion lubricant additive product of reaction having the following generalized structure:

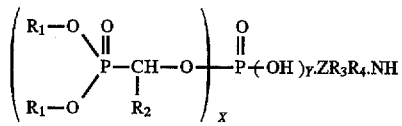

where x is 1 to 2, and x+y=3, Z is any natural number $0 \leq Z \leq 100$; $R_3$ and $R_4$ are hydrogen or $C_1$ to $C_{60}$ hydrocarbyl which optionally contain at least one heteroatom selected from a member of the group consisting of nitrogen, sulfur, or oxygen; and wherein $R_1$ is $C_1$ to about $C_{60}$ hydrocarbyl; $R_2$ is hydrogen or $C_1$ to about $C_{30}$ hydrocarbyl, x is 1 to 2, and x+y=3.

24. A method of preparing an improved lubricant composition comprising adding to said lubricant a minor multifunctional antiwear/antioxidant amount of from about 0.001 to about 10 wt % based on the total weight of the composition of an additive product of reaction as described in claim 19.

25. The process as recited in claim 15 where a catalyst is utilized that is selected from a member of the group consisting of sodium hydroxide, potassium hydroxide, calcium hydroxide, or lithium hydroxide, or any other basic and/or nucleophilic species.

* * * * *